(12) United States Patent
Byrne et al.

(10) Patent No.: US 9,608,455 B2
(45) Date of Patent: Mar. 28, 2017

(54) WIRELESS POWER FOR PORTABLE ARTICLES

(71) Applicants: Norman R. Byrne, Ada, MI (US);
Robert L. Knapp, Rockford, MI (US);
Timothy J. Warwick, Sparta, MI (US);
Roger D. Burdi, Grand Rapids, MI (US)

(72) Inventors: Norman R. Byrne, Ada, MI (US);
Robert L. Knapp, Rockford, MI (US);
Timothy J. Warwick, Sparta, MI (US);
Roger D. Burdi, Grand Rapids, MI (US)

(*) Notice: Subject to any disclaimer, the term of this patent is extended or adjusted under 35 U.S.C. 154(b) by 0 days.

(21) Appl. No.: 15/335,535

(22) Filed: Oct. 27, 2016

(65) Prior Publication Data

US 2017/0047780 A1 Feb. 16, 2017

Related U.S. Application Data

(63) Continuation of application No. 14/501,158, filed on Sep. 30, 2014, now Pat. No. 9,484,751.

(60) Provisional application No. 61/884,171, filed on Sep. 30, 2013.

(51) Int. Cl.
*H01F 37/00* (2006.01)
*H02J 5/00* (2016.01)
*H02J 7/02* (2016.01)

(52) U.S. Cl.
CPC .............. *H02J 5/005* (2013.01); *H02J 7/025* (2013.01)

(58) Field of Classification Search
CPC .............. H02J 5/005; H02J 7/025; H02J 17/00
USPC ........................................................ 307/104
See application file for complete search history.

(56) References Cited

U.S. PATENT DOCUMENTS

| 5,171,159 | A | 12/1992 | Byrne |
| 5,575,668 | A | 11/1996 | Timmerman |
| 5,959,433 | A | 9/1999 | Rohde |
| 6,028,267 | A | 2/2000 | Byrne |
| 6,028,413 | A | 2/2000 | Brockmann |
| 6,036,516 | A | 3/2000 | Byrne |
| 6,290,518 | B1 | 9/2001 | Byrne |
| 6,379,182 | B1 | 4/2002 | Byrne |

(Continued)

FOREIGN PATENT DOCUMENTS

| CN | 202552802 | 11/2012 |
| WO | 2013/112185 | 8/2013 |

*Primary Examiner* — Jared Fureman
*Assistant Examiner* — Alfonso Perez Borroto
(74) *Attorney, Agent, or Firm* — Gardner, Linn, Burkhart & Flory, LLP

(57) ABSTRACT

A wireless electrical power system provides access to high voltage and/or low voltage electrical power at portable articles that are positionable at different locations within a work area, and substantially without the use of exposed cabling. The power system includes a portable article that is positionable at two or more locations within a work area. The work area is defined by a plurality of surfaces, at least one of which incorporates a wireless electrical power transmitter. The portable article incorporates a wireless electrical power receiver that is configured to receive electrical power from the wireless power transmitter when the wireless power receiver is sufficiently close to the wireless power transmitter. The portable article further includes an electrical power outlet that provides users in the work area with access to the electrical power.

19 Claims, 19 Drawing Sheets

(56) References Cited

U.S. PATENT DOCUMENTS

| | | |
|---|---|---|
| 6,436,299 B1 | 8/2002 | Baarman et al. |
| 6,756,697 B2 | 6/2004 | Mizutani et al. |
| 6,803,744 B1 | 10/2004 | Sabo |
| 6,967,462 B1 | 11/2005 | Landis |
| 7,183,504 B2 | 2/2007 | Byrne |
| 7,212,414 B2 | 5/2007 | Baarman |
| 7,222,031 B2 | 5/2007 | Heatley |
| 7,233,222 B2 | 6/2007 | Baarman et al. |
| 7,262,700 B2 | 8/2007 | Hsu |
| 7,355,150 B2 | 4/2008 | Baarman et al. |
| 7,392,068 B2 | 6/2008 | Dayan et al. |
| 7,399,202 B2 | 7/2008 | Dayan et al. |
| 7,443,057 B2 | 10/2008 | Nunally |
| 7,465,178 B2 | 12/2008 | Byrne |
| 7,633,263 B2 | 12/2009 | Toya |
| 7,736,178 B2 | 6/2010 | Byrne |
| 7,863,861 B2 | 1/2011 | Cheng et al. |
| 7,878,845 B2 | 2/2011 | Byrne |
| 7,887,113 B2 | 2/2011 | Lambarth et al. |
| 8,061,864 B2 | 11/2011 | Metcalf et al. |
| 8,106,539 B2 | 1/2012 | Schatz et al. |
| 8,262,244 B2 | 9/2012 | Metcalf et al. |
| 8,283,812 B2 | 10/2012 | Azancot et al. |
| 8,295,036 B2 | 10/2012 | Byrne |
| 8,395,353 B2 | 3/2013 | Wang et al. |
| 8,398,408 B1 | 3/2013 | Hansen et al. |
| 8,421,407 B2 | 4/2013 | Johnson |
| 8,444,432 B2 | 5/2013 | Byrne et al. |
| 8,456,038 B2 | 6/2013 | Azancot et al. |
| 8,480,429 B2 | 7/2013 | Byrne |
| 8,482,160 B2 | 7/2013 | Johnson et al. |
| 8,487,478 B2 | 7/2013 | Kirby et al. |
| 8,497,601 B2 | 7/2013 | Hall et al. |
| 8,558,661 B2 | 10/2013 | Zeine |
| 8,559,172 B2 | 10/2013 | Byrne |
| 8,581,444 B2 | 11/2013 | Urano |
| 8,618,695 B2 | 12/2013 | Azancot et al. |
| 8,624,750 B2 | 1/2014 | Azancot |
| 8,721,124 B2 | 5/2014 | Byrne et al. |
| 8,937,407 B2 | 1/2015 | Byrne et al. |
| 8,951,054 B2 | 2/2015 | Byrne et al. |
| 9,148,006 B2 | 9/2015 | Byrne et al. |
| 9,438,070 B2 | 9/2016 | Byrne et al. |
| 2002/0171335 A1 | 11/2002 | Held |
| 2003/0048254 A1 | 3/2003 | Huang |
| 2003/0202317 A1 | 10/2003 | Jans |
| 2004/0026998 A1 | 2/2004 | Henriott et al. |
| 2004/0150934 A1 | 8/2004 | Baarman |
| 2004/0189246 A1 | 9/2004 | Bulai et al. |
| 2007/0182367 A1 | 8/2007 | Partovi |
| 2007/0279002 A1 | 12/2007 | Partovi |
| 2008/0001572 A9 | 1/2008 | Baarman et al. |
| 2008/0079392 A1 | 4/2008 | Baarman et al. |
| 2008/0166965 A1 | 7/2008 | Greene et al. |
| 2008/0169910 A1 | 7/2008 | Greene et al. |
| 2008/0200050 A1 | 8/2008 | Byrne |
| 2009/0045772 A1 | 2/2009 | Cook et al. |
| 2009/0212636 A1 | 8/2009 | Cook et al. |
| 2009/0212638 A1 | 8/2009 | Johnson |
| 2009/0230777 A1 | 9/2009 | Baarman et al. |
| 2009/0271048 A1 | 10/2009 | Wakamatsu |
| 2009/0278494 A1 | 11/2009 | Randall |
| 2010/0007307 A1 | 1/2010 | Baarman et al. |
| 2010/0038970 A1 | 2/2010 | Cook et al. |
| 2010/0052431 A1 | 3/2010 | Mita |
| 2010/0127660 A1 | 5/2010 | Cook et al. |
| 2010/0187913 A1 | 7/2010 | Smith et al. |
| 2010/0201201 A1 | 8/2010 | Mobarhan et al. |
| 2010/0244584 A1 | 9/2010 | Azancot et al. |
| 2010/0259401 A1 | 10/2010 | Azancot et al. |
| 2010/0290215 A1 | 11/2010 | Metcalf et al. |
| 2010/0308665 A1* | 12/2010 | Itkonen ............... H02J 5/005 307/104 |
| 2010/0321939 A1 | 12/2010 | Patel |
| 2011/0006611 A1 | 1/2011 | Baarman et al. |
| 2011/0062789 A1 | 3/2011 | Johnson et al. |
| 2011/0121660 A1 | 5/2011 | Azancot et al. |
| 2011/0175544 A1 | 7/2011 | Jong |
| 2011/0193417 A1 | 8/2011 | Hirasaka et al. |
| 2011/0241607 A1 | 10/2011 | Wiegers |
| 2011/0241614 A1 | 10/2011 | Yeh |
| 2011/0248575 A1 | 10/2011 | Kim et al. |
| 2011/0260548 A1 | 10/2011 | Urano |
| 2011/0305056 A1 | 12/2011 | Chien |
| 2012/0113576 A1 | 5/2012 | Cooper et al. |
| 2012/0113645 A1 | 5/2012 | Liao et al. |
| 2012/0117730 A1 | 5/2012 | Lemire et al. |
| 2012/0153731 A9 | 6/2012 | Kirby et al. |
| 2012/0206097 A1 | 8/2012 | Soar |
| 2012/0228953 A1 | 9/2012 | Kesler et al. |
| 2012/0235474 A1 | 9/2012 | Mannino et al. |
| 2012/0261998 A1 | 10/2012 | Sato |
| 2012/0299539 A1 | 11/2012 | Jones et al. |
| 2012/0312196 A1 | 12/2012 | Newkirk |
| 2013/0049482 A1 | 2/2013 | Rofe et al. |
| 2013/0057203 A1 | 3/2013 | Jones et al. |
| 2013/0141038 A1 | 6/2013 | Papa |
| 2013/0175986 A1 | 7/2013 | Senatori |
| 2013/0200717 A1 | 8/2013 | Bourilkov et al. |
| 2013/0207478 A1 | 8/2013 | Metcalf et al. |
| 2013/0234481 A1 | 9/2013 | Johnson |
| 2013/0285606 A1 | 10/2013 | Ben-Shalom et al. |
| 2014/0361633 A1 | 12/2014 | Abe |

\* cited by examiner

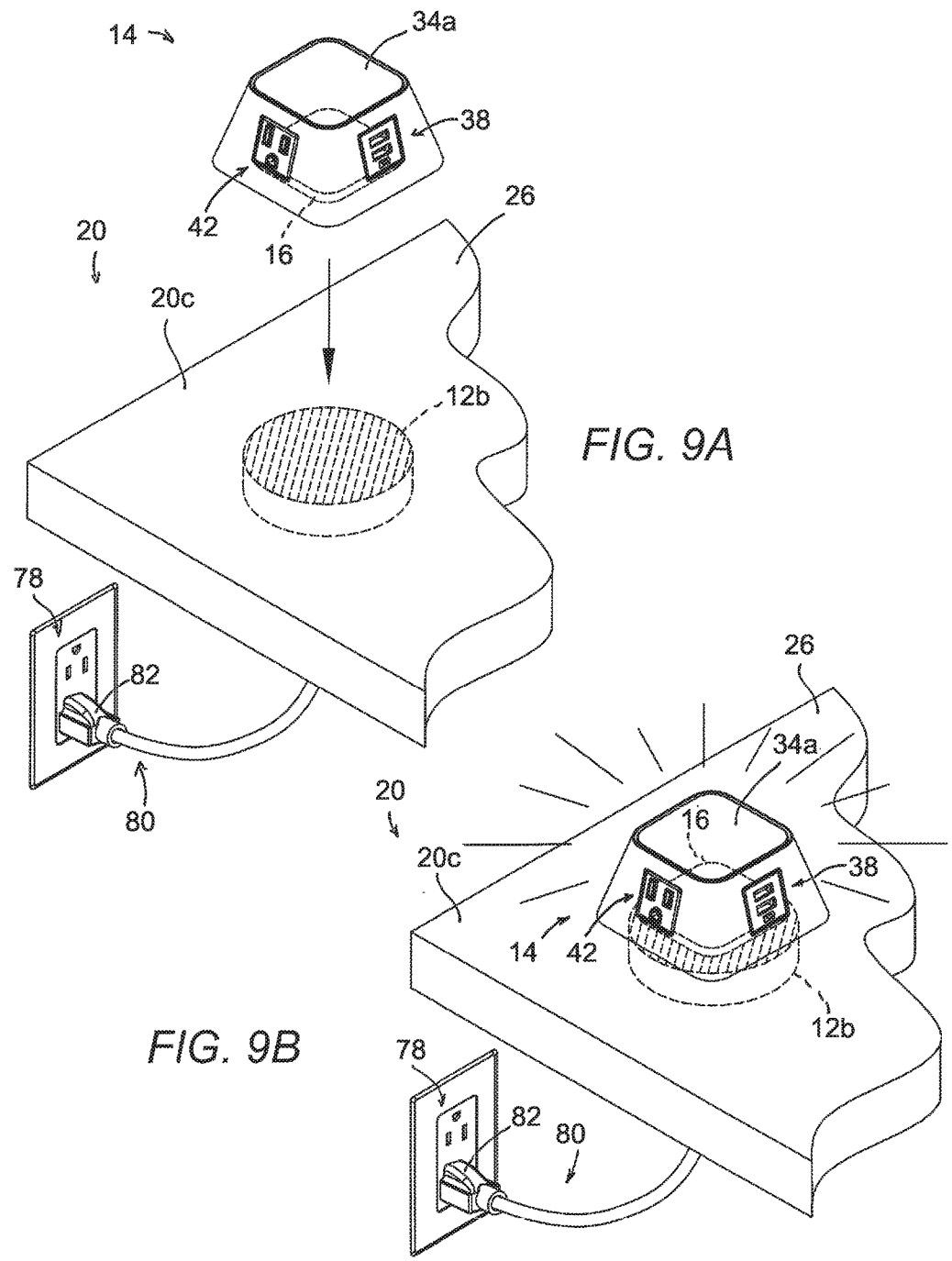

WIRELESS POWER FOR PORTABLE ARTICLES

CROSS REFERENCE TO RELATED APPLICATION

The present application is a continuation of U.S. patent application Ser. No. 14/501,158, filed Sep. 30, 2014, which claims the benefit of U.S. provisional application Ser. No. 61/884,171, filed Sep. 30, 2013, both of which are hereby incorporated herein by reference in their entireties.

FIELD OF THE INVENTION

The present invention relates to electrical power systems for providing users with access to electrical power within a work area.

BACKGROUND OF THE INVENTION

Electrical power receptacles or outlets are commonly located in work areas, such as at or near work surfaces, in walls, in floors, and in ceilings. However, electrical power receptacles that are located remotely from walls, floors, or ceilings typically require exposed cords or wiring that can create a trip hazard or limit access to certain areas of the work area, can become tangled, and can result in partially-exposed electrical contacts within the work area. In addition, the typical need to establish direct electrical connections increases the effort required to move electrical receptacles, and is limited by the length of wiring that is readily available, as well as the routing paths available for such wiring.

SUMMARY OF THE INVENTION

The present invention provides a wireless power system for use in a work area, such as in an office, a home, a hotel, an airport or other transit station, a vehicle, or the like. The wireless power system includes at least one wireless power transmitter and at least one wireless power receiver, the receiver being located at a portable article such as an article of furniture or a device that is supportable on a work surface such as a table or a desk. The portable article includes at least one electrical power receptacle or outlet such as a low-voltage DC receptacle or outlet, a high-voltage AC receptacle or outlet, a light socket, a low voltage charging pad, or a wireless power transmitter, in order to provide users in the work area with access to electrical power via the portable article.

According to one aspect of the present invention, a wireless power system includes a wireless electrical power transmitter, a portable article, a wireless electrical power receiver, and an electrical power receptacle or outlet. The wireless electrical power transmitter is disposed in a surface that defines a portion of a work area. Such surfaces may include, for example, a wall surface, a floor surface, a work surface, and a ceiling surface. The portable article is configured to be positioned within the work area, and is movable between two or more locations in the work area. The wireless electrical power receiver is positioned at the portable article and is configured to receive electrical power from the wireless electrical power transmitter when the wireless electrical power receiver is adjacent or spaced from the wireless electrical power transmitter by a distance that is less than or equal to a maximum transmission distance. The electrical power receptacle or outlet is positioned at the portable article and is configured to receive electrical power from the wireless electrical power receiver, and to provide electrical power to an electrical consumer that is electrically coupled to the electrical power receptacle or outlet.

In one aspect, the wireless electrical power transmitter is an inductive power transmitter that receives electrical power from a main power source, such as via electrical wiring.

In another aspect, the portable article is an article of furniture, such as a chair, a table, a desk, a cart, or a cabinet. Optionally, the furniture article is supported on a plurality of wheels or rollers. Optionally, the portable article includes a wireless electrical power transmitter that is configured to provide electrical power to another electrical power receiver of another portable article, such as a furniture article.

In a further aspect, the portable article includes an electrical energy storage device that is operable to supply electrical current to the electrical power receptacle, such as at times when the wireless electrical power receiver is not receiving power from the wireless electrical power transmitter. Optionally, the electrical energy storage device receives electrical energy from the wireless electrical power receiver. The electrical energy storage device may be a rechargeable battery, for example.

In still another aspect, the portable article is an electrical device that is configured to be supported on a work surface. For example, the electrical device may be a power monument or an electric lamp.

In yet another aspect, the electrical power receptacle includes at least one of: a low-voltage DC receptacle or outlet, a high-voltage AC receptacle or outlet, a light socket, and a low voltage charging pad.

Thus, the wireless power system of the present invention provides users of a work area with access to electrical power at different locations within the area, and allows the area to be reconfigured according to the desired types and locations of furniture, as well as the desired types and locations of electrical receptacles or outlets or wireless power connections, but without requiring cabling or wiring to extend through the work area, and without the need to establish direct contact electrical connections. This permits high and/or low voltage power to be provided throughout a work area, which can be used for powering or charging hand-held electronics, lighting, appliances, or the like, while facilitating the rapid reconfiguration of furnishings and power connections in the work area.

These and other objects, advantages, purposes and features of the present invention will become apparent upon review of the following specification in conjunction with the drawings.

BRIEF DESCRIPTION OF THE DRAWINGS

FIG. 9A is a perspective view of a portable tabletop power monument shown spaced above a work surface incorporating a wireless power transmitter, in accordance with the present invention;

FIG. 9B is another perspective view of the power monument and work surface of FIG. 9A, in which the power monument is positioned at the work surface above the wireless power transmitter;

DESCRIPTION OF THE PREFERRED EMBODIMENTS

Figure 1A:
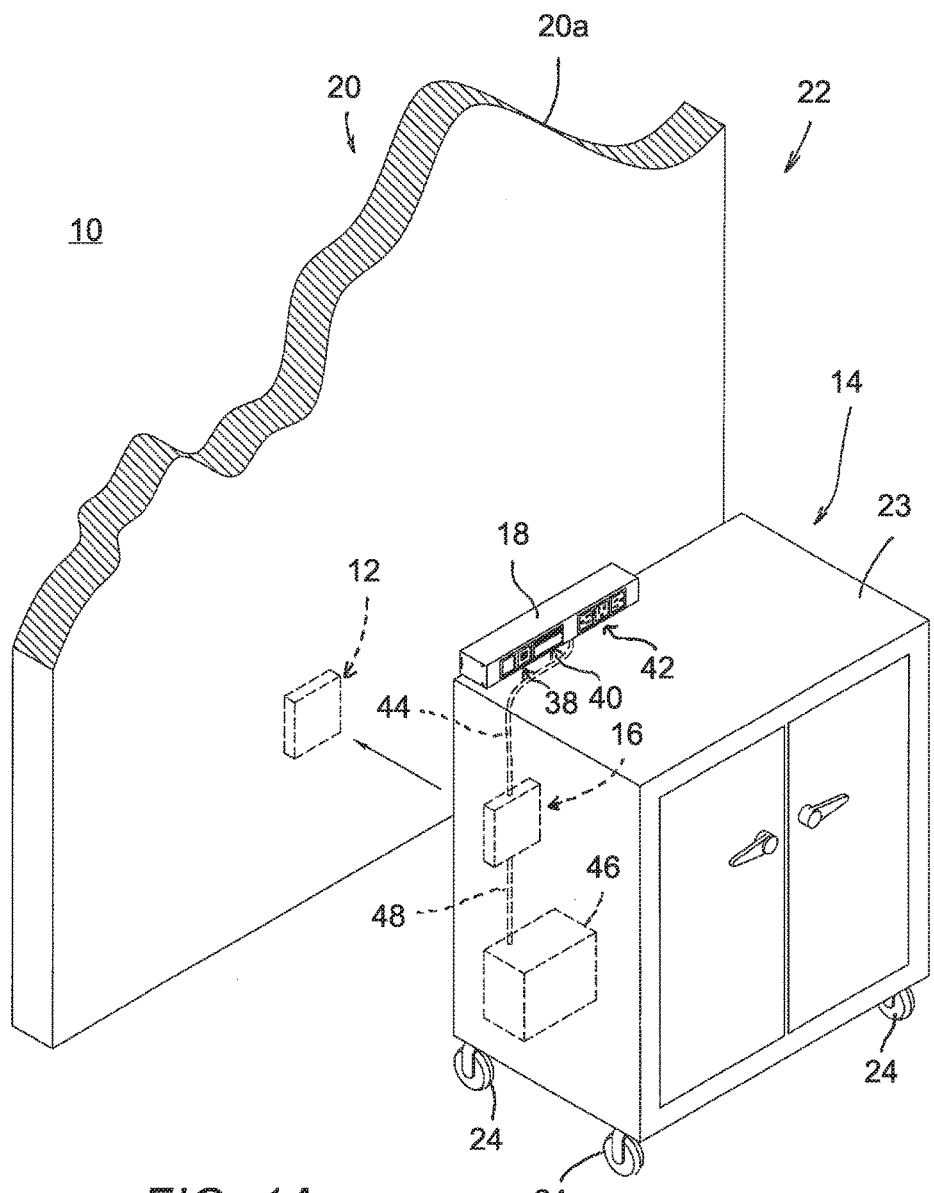
FIG. 1A is a perspective view of a mobile storage cart with wireless power in accordance with the present invention, shown spaced from a wall surface that is equipped with a wireless power transmitter.
Figure 1B:
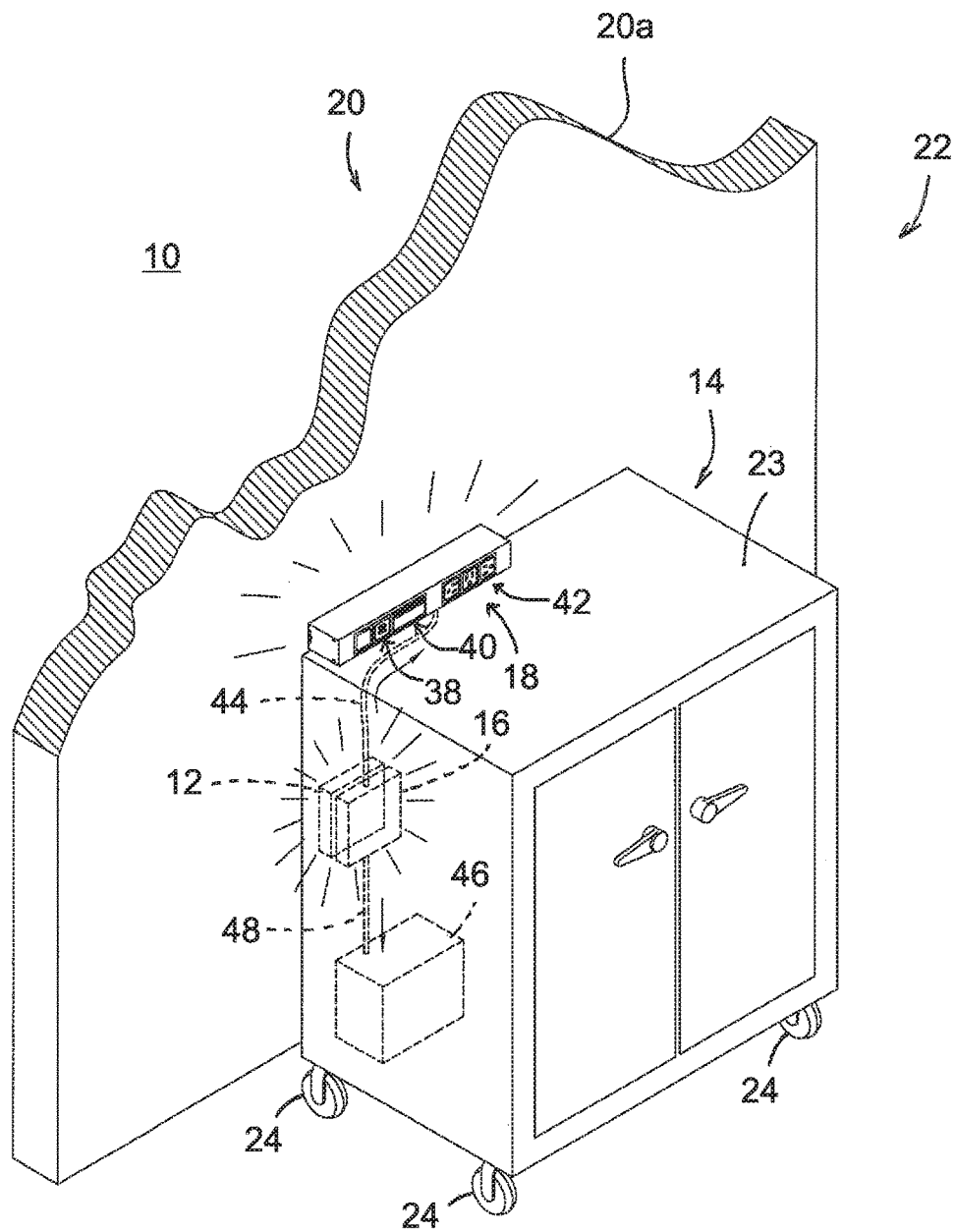
FIG. 1B is another perspective view of the mobile storage cart and wall surface of FIG. 1A, in which the cart is moved to be adjacent the wall surface.

A wireless power system facilitates the placement and relocation of electrical receptacles and/or devices within a work area, while reducing or eliminating the need for exposed electrical cords and simplifying the procedure for relocating the electrical devices or articles that contain electrical receptacles or outlets or access points. Referring now to the drawings and the illustrative embodiments depicted therein, a wireless electrical power system 10 includes a wireless electrical power transmitter 12, a portable article 14 such as an article of furniture or an electrical device, a wireless electrical power receiver 16, and an electrical power receptacle or outlet unit 18 at the portable article 14 (FIGS. 1A and 1B). The wireless electrical power transmitter 12 is typically mounted in a surface 20 that defines a portion of a work area 22. Examples of different types of surfaces 20 that may incorporate power transmitters 12 include a wall surface 20a (FIGS. 1A, 1B, 3A, 3B, and 5A-6B) that may be a fixed or movable panel or wall or divider of full or partial height, a floor surface 20b (FIGS. 2A-2C, 4A, 4B, and 7A-8B), a work surface 20c (FIGS. 9A-10B), and a ceiling surface 20d (FIGS. 6A and 6B), so that any of these surfaces may act as a wireless power source for electrical outlets, receptacles, or power consumers within the work area 22.

Figure 6A:
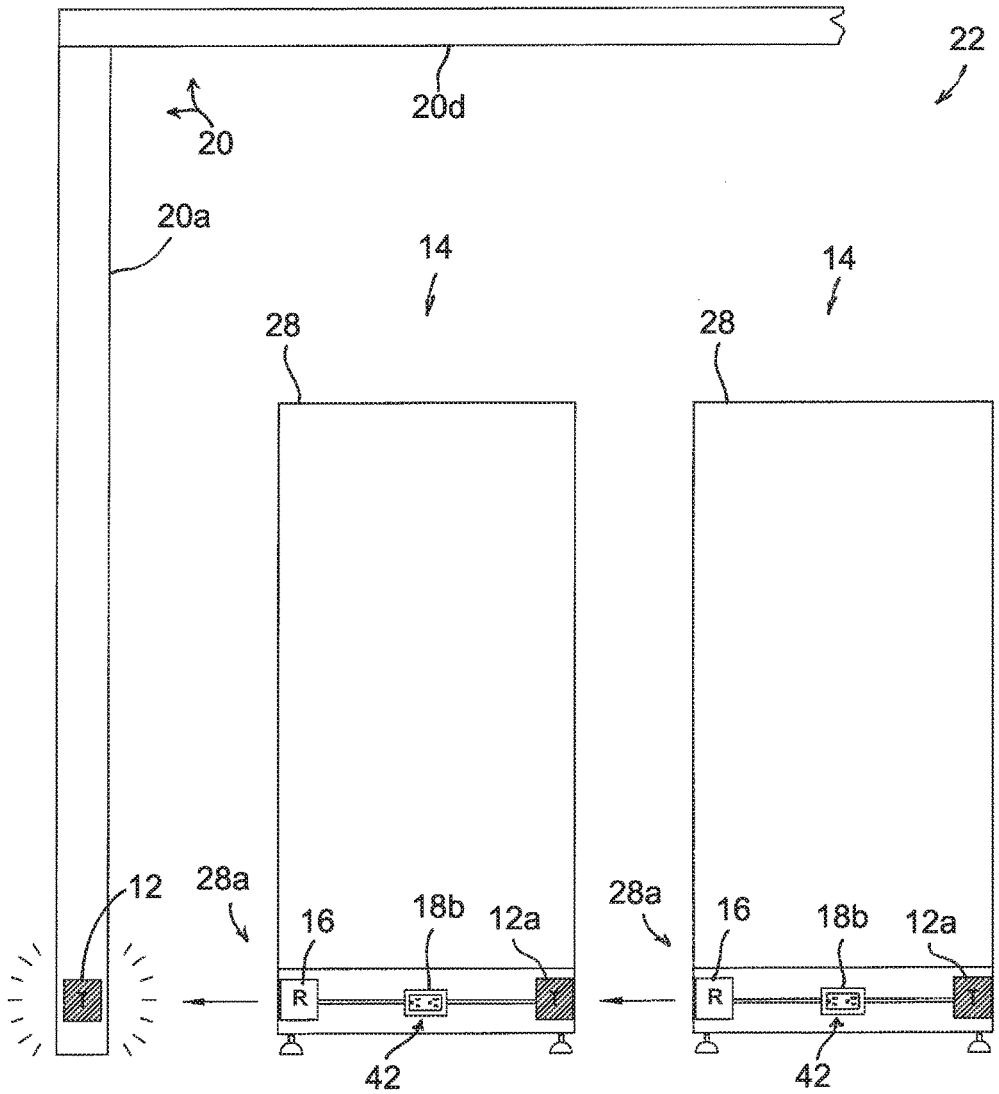
FIG. 6A is a side elevation diagram of a pair of movable cabinets equipped with wireless power receivers and wired power outlets and transmitters in accordance with the present invention, shown spaced from a wall surface that is equipped with a wireless power transmitter.
Figure 6B:
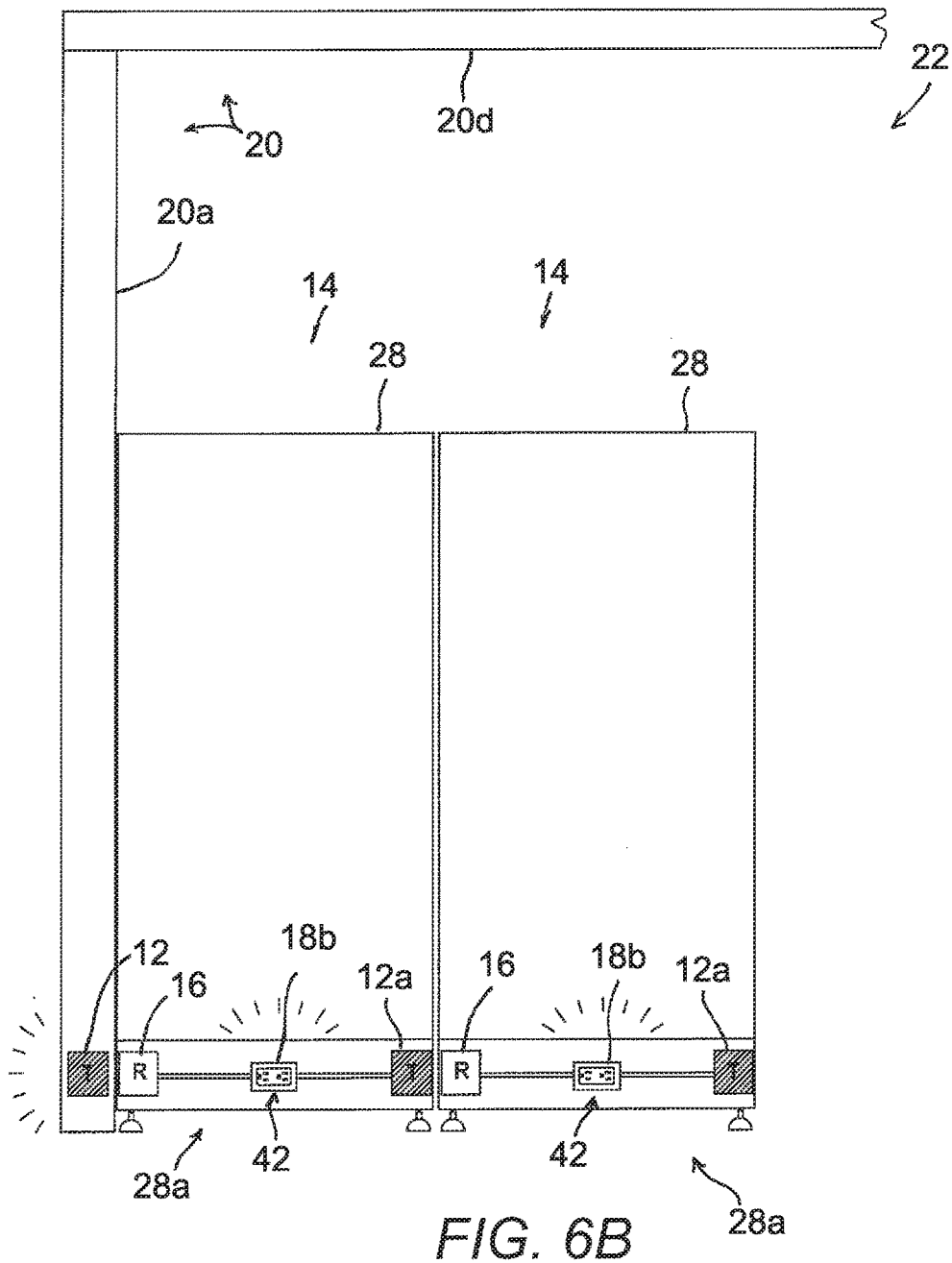
FIG. 6B is another side elevation diagram of the movable cabinets and wall surface of FIG. 6A, in which the cabinets are moved to be adjacent one another and one of the cabinets is adjacent the wall surface.
Figure 7A:
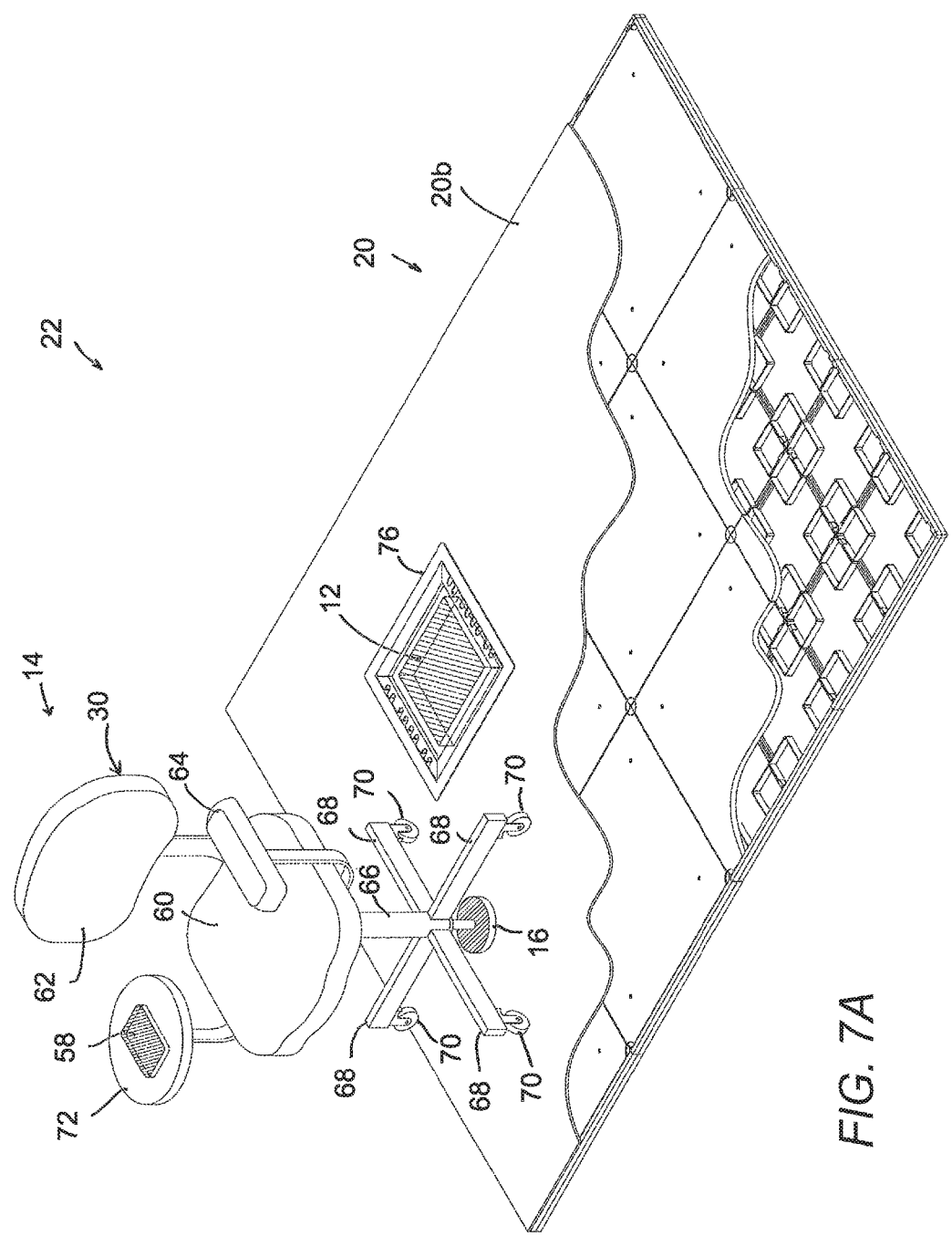
FIG. 7A is a perspective view of a mobile office chair with wireless power in accordance with the present invention, shown positioned along a floor surface and spaced from a wireless power transmitter in the floor surface.
Figure 7B:
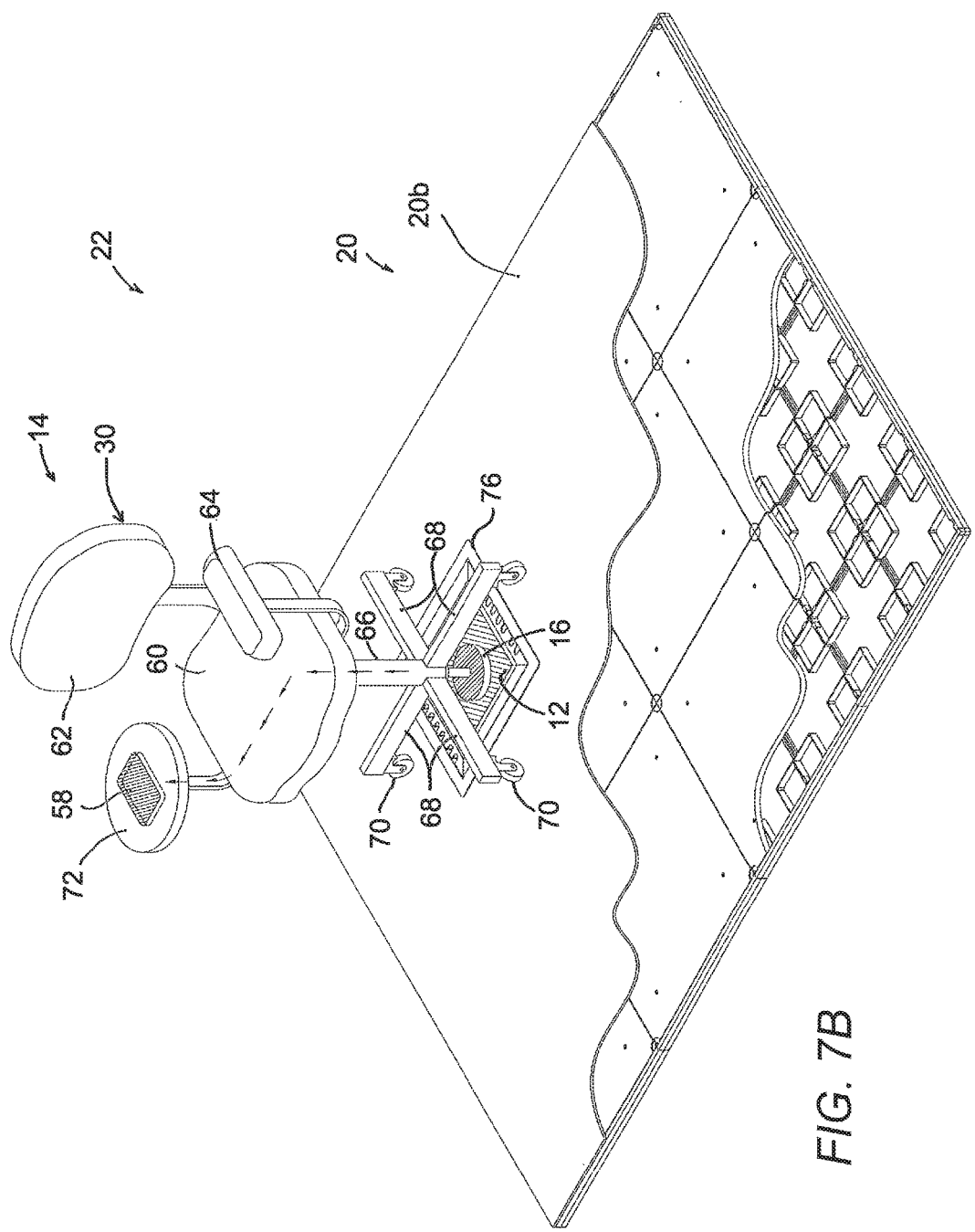
FIG. 7B is another perspective view of the office chair and floor surface of FIG. 7A, in which the chair is aligned with the wireless power transmitter in the floor surface.
Figure 10A:
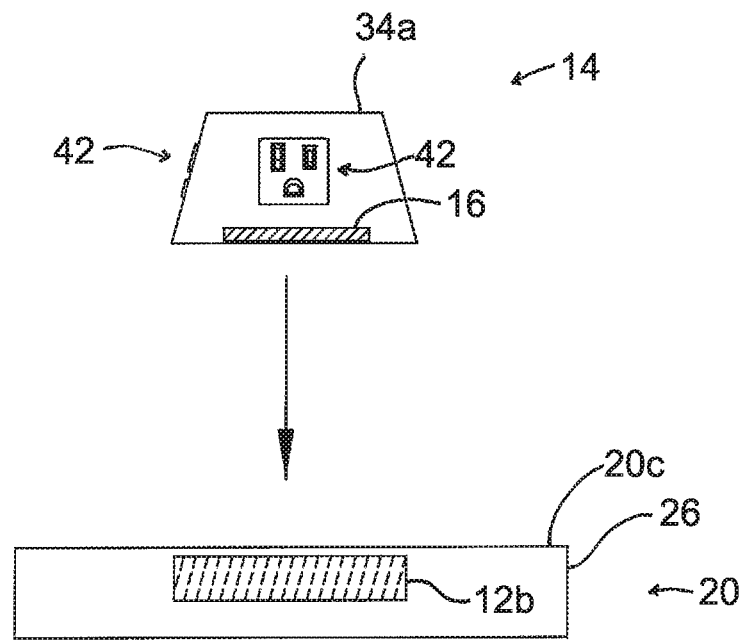
FIG. 10A is a side elevation of the power monument and work surface of FIG. 9A.
Figure 10B:
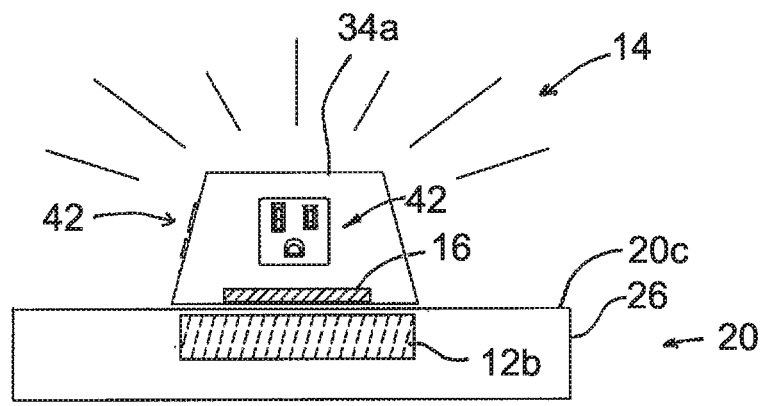
FIG. 10B is a side elevation of the power monument and work surface of FIG. 9B.
Figure 11A:
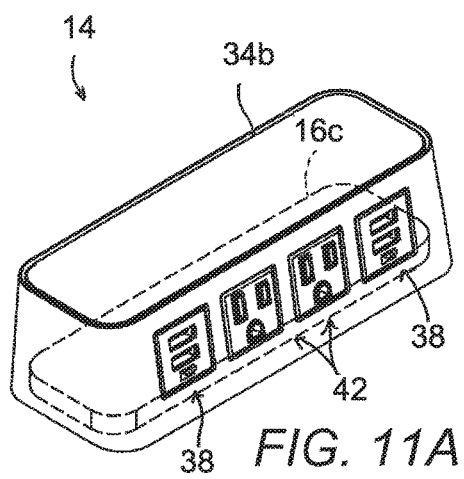
FIG. 11A is a perspective view of another portable tabletop power monument having an elongated rectangular shape.
Figure 11B:
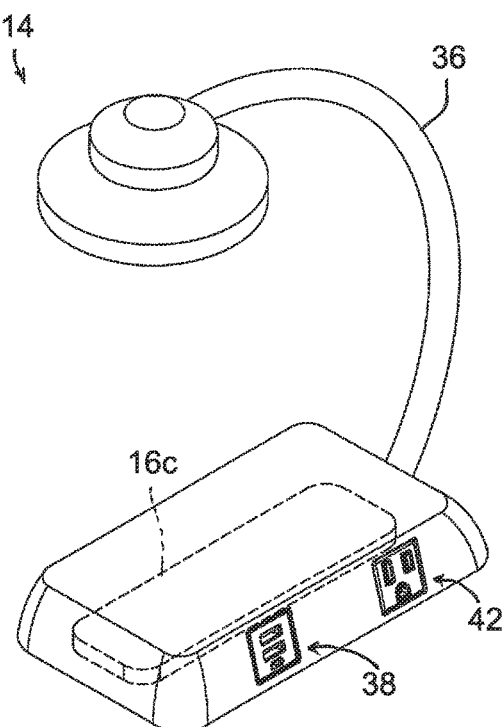
FIG. 11B is a perspective view of a portable lamp with power outlets.

Portable articles 14 may be substantially any furniture article or device that is movable or repositionable between two or more locations within work area 22. For example, and as shown in FIGS. 1A-2C, portable article 14 may be a rolling cart 23 that includes a set of wheels 24 to facilitate movement of the cart along floor surface 20b (FIGS. 2A and 2B). Optionally, the portable article may be another type of furniture, such as a desk or table 26 (FIGS. 3A-5B), a cabinet 28 (FIGS. 6A and 6B), or a chair 30 (FIGS. 7A and 7B). However, it is further envisioned that portable articles 14 may include electrical or electrically-equipped devices that are supportable on a floor surface or a work surface. For example, portable articles 14 may include a floor-supported electrified column or tower 32 (FIGS. 8A and 8B), a table-supportable electrified monument 34a, 34b (FIGS. 9A-11A), and an electric portable lamp 36 (FIG. 11B).

Wireless electrical power transmitter 12 may be hidden from view within substantially any fixed or movable or repositionable surface 20, or may be exposed or mounted external to the surface 20 within the work area 22. It will be appreciated that work area 22 is representative of substantially any task area, including areas that may be located in an office, a home, a hotel, an airport or other transit station, a vehicle, or the like. Optionally, power transmitter 12 is an inductive power transmitter or coupling that receives electrical power from wiring (e.g., routed through walls, flooring, ceiling, raceways, etc.) that is coupled to a power source associated with the building, structure, or vehicle in which portable article 14 is located. Alternatively, power transmitter 12 may be a direct-contact power transmitter, for example a high voltage AC power transmitter (e.g., a conventional AC wall outlet or floor outlet) or a low voltage DC power transmitter, of which a low voltage DC power transmitter is described in commonly-owned U.S. provisional application Ser. No. 62/022,740, filed Jul. 10, 2014, which is hereby incorporated herein by reference in its entirety.

When power transmitter 12 is hidden within a given surface 20, it may be desirable to mark the surface with some form of indicia that is indicative of the location of the power transmitter, so that a user desiring to move an article 14 to a location where its corresponding wireless electrical power receiver 16 will be in electrical communication with power transmitter 12, can readily identify the location of the power transmitter(s) within work area 22. Surface 20 may be fixed in place, or may be movable within or relative to the work area, such as a pivoting or sliding partial or full wall or divider, which may allow for power transmitter 12 to be moved toward power receiver 16 of portable article 14 to thereby establish a wireless electrical coupling.

Figure 1C:
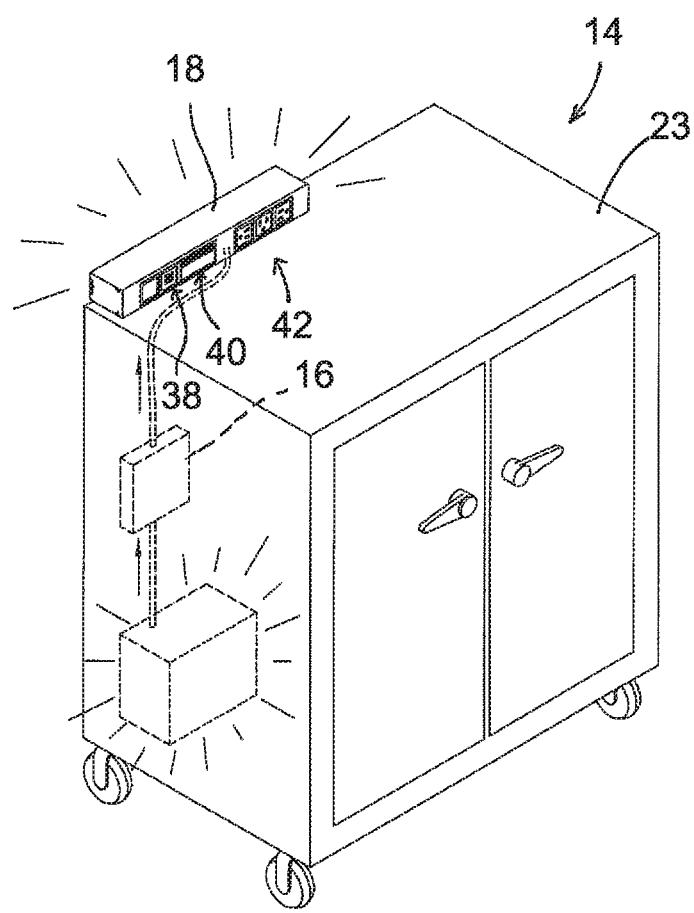
FIG. 1C is a perspective view of the mobile storage cart of FIGS. 1A and 1B, in which the cart is operating in a self-powered mode.
Figure 2A:
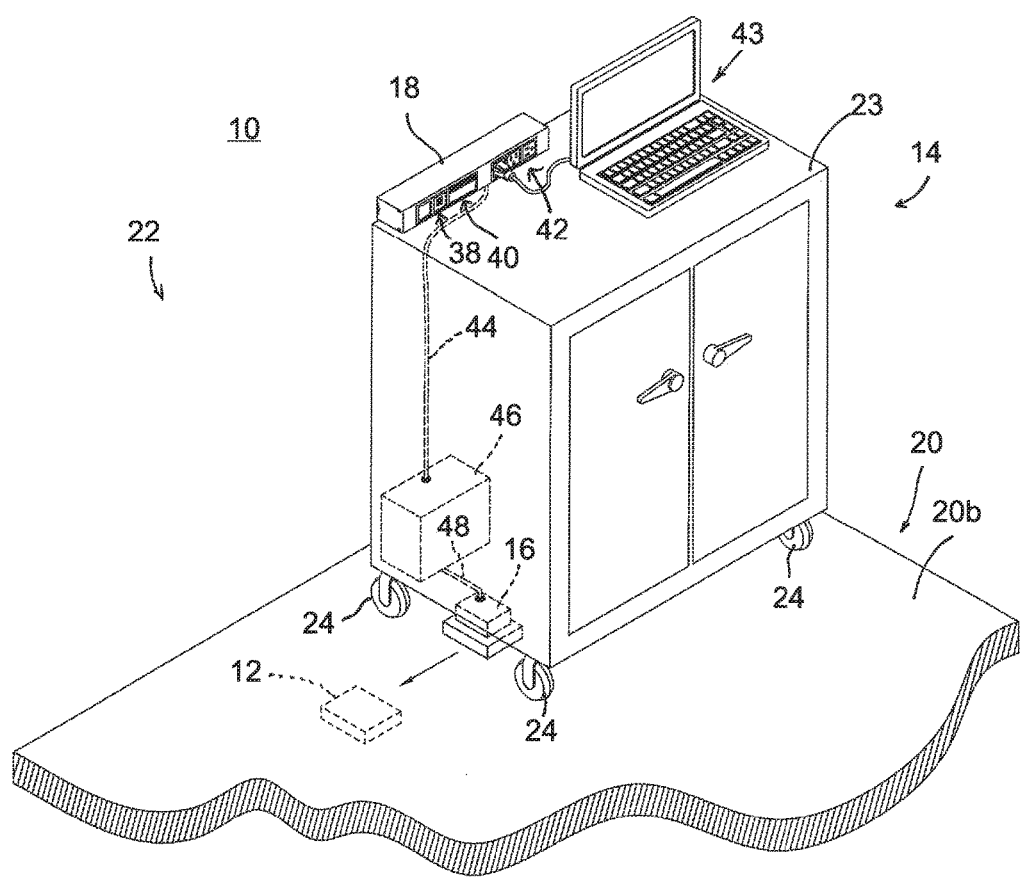
FIG. 2A is a perspective view of another mobile storage cart with wireless power in accordance with the present invention, shown positioned along a floor surface and spaced from a wireless power transmitter in the floor surface.
Figure 2B:
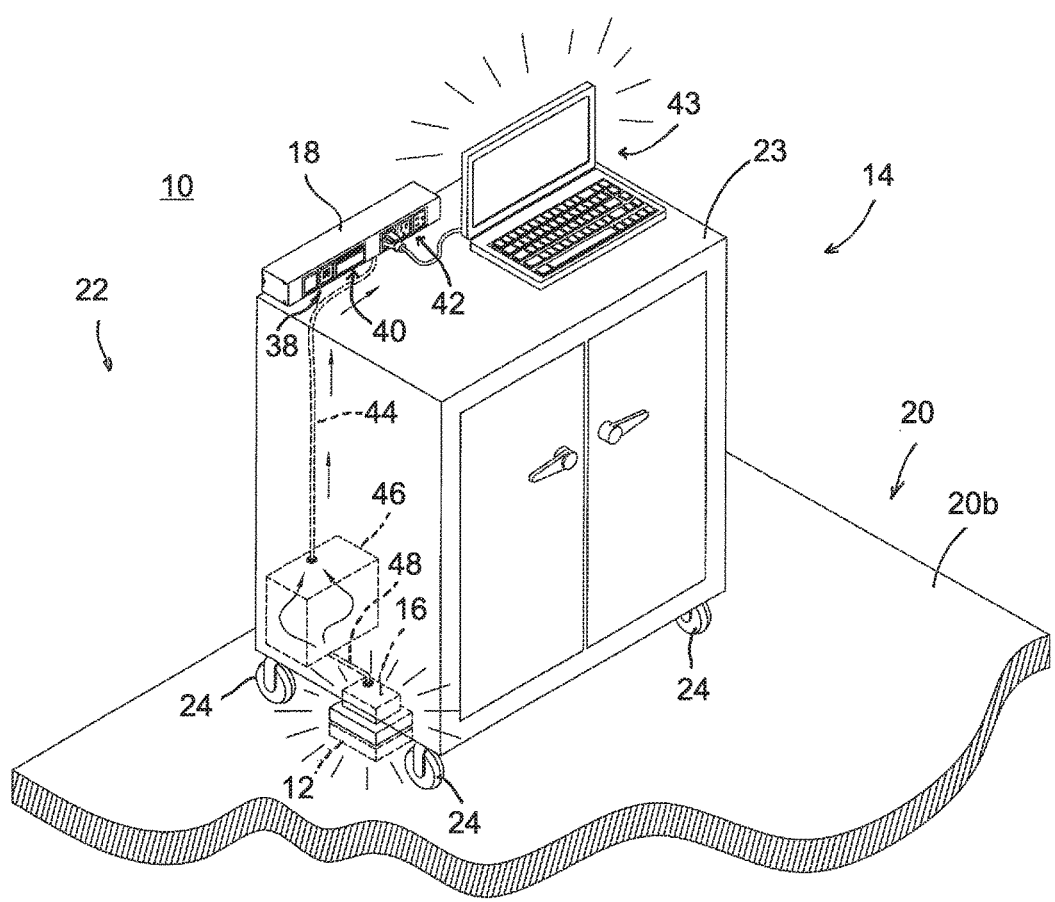
FIG. 2B is another perspective view of the mobile storage cart and floor surface of FIG. 2A, in which the cart is moved to align with the wireless power transmitter in the floor surface.
Figure 2C:
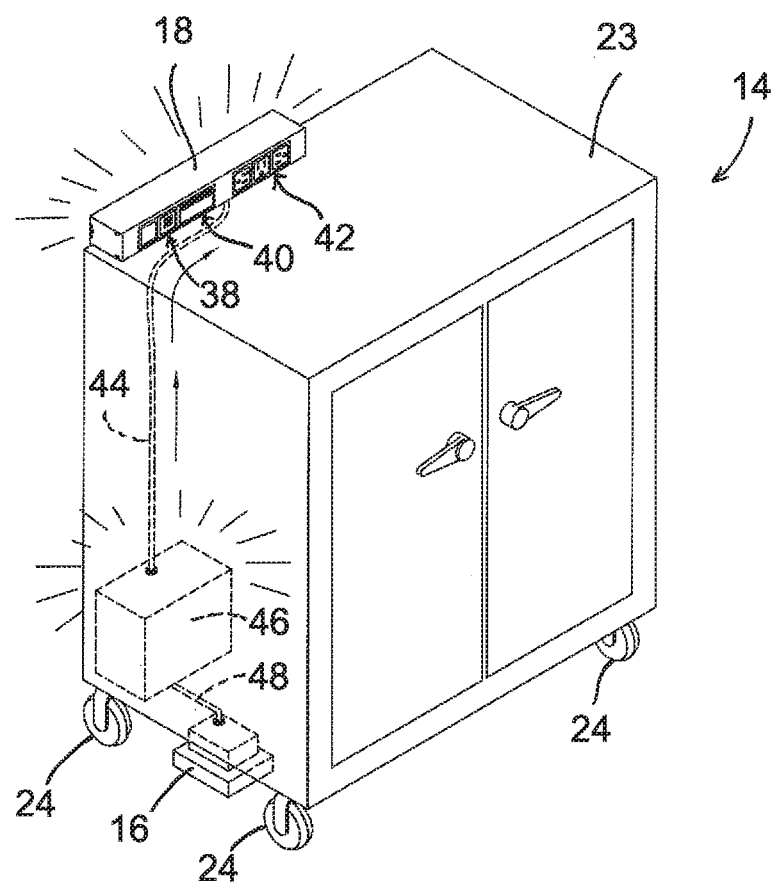
FIG. 2C is another perspective view of the mobile storage cart of FIGS. 2A and 2B, in which the cart is operating in a self-powered mode.

In the illustrated embodiments of FIGS. 1A-2C, wireless electrical power receiver 16 is positioned inside of rolling cart 23, along a rear surface thereof, and is spaced above a floor surface by approximately the same distance that power transmitter 12 is spaced above the same floor surface. In this arrangement, rolling cart 23 may be moved into close proximity to wall surface 20a so that power receiver 16 is substantially aligned with power transmitter 12, thus creating a wireless power coupling between the receiver and transmitter. Optionally, power receiver 16 may be mounted externally on cart 23, such as shown in FIGS. 2A-2C. It will be appreciated that, regardless of the location of power receiver 16, an effective wireless power coupling occurs when the wireless electrical power receiver 16 is spaced from the wireless electrical power transmitter 12 by a distance that is less than or equal to a maximum transmission distance for the particular transmitter and receiver combination.

In addition to power receiver 16, rolling cart 23 supports power receptacle or outlet unit 18 along an upper surface thereof, although it will be appreciated that the power receptacle or outlet unit 18 (or single receptacles or separate groups of receptacles or outlets) may be positioned substantially anywhere along the exterior or the interior of cart 23, without departing from the spirit and scope of the present invention. In the illustrated embodiment of FIGS. 1A-2C, power receptacle unit 18 includes low-voltage (such as USB-style) DC receptacles 38, a low-voltage charging base 40, and high-voltage AC receptacles or outlets 42, and the like. Examples of suitable power receptacle units and receptacles are described in more detail in commonly-owned U.S. Pat. Nos. 6,379,182; 8,444,432; 8,480,429; and 8,559,172, all of which are hereby incorporated herein by reference in their entireties.

The electrical power receptacle or outlet unit 18 provides electrical power to one or more electrical consumers that may be located at or near portable article 14 (such as rolling cart 23). Electrical consumers may include, for example, a laptop computer 43 (FIGS. 2A and 2B), a mobile phone, handheld computer or other rechargeable device, lighting, electrical appliances, or the like, which may be electrically coupled (via wired or wireless coupling) to the electrical power receptacles of electrical power receptacle unit 18. In the illustrated embodiments, power receptacle unit 18 is electrically coupled to power receiver 16 and supplied with power via electrical wiring 44. Electrical wiring 44 may include only high voltage AC wiring, so that one or more power transformers in power receptacle unit 18 convert the incoming high voltage received from power receiver 16 to a lower voltage DC power output at DC receptacles 38 and/or charging base 40. Optionally, electrical wiring 44 may include both high voltage AC wiring and low voltage DC wiring that is coupled to respective receptacles at power receptacle unit 18.

Rolling cart 23 further contains an optional electrical energy storage device 46 that can supply electrical current to the electrical power receptacle unit 18 for a limited time before storage device 46 requires replacement or recharging. Storage device 46 is electrically coupled to power receiver 16 via wiring 48, which may be used both to supply electrical power from power receiver 16 to storage device 46, and to supply electrical power to power receptacle unit 18 via power receiver 16 and wiring 44. For example, storage device 46 may be a rechargeable battery having a low voltage DC output, such as about 24V DC or less, so that an electrical transformer or inverter (e.g., mounted at any of power receiver 16, power receptacle unit 18, or storage device 46) may be used to convert the DC output of storage device 46 to a high voltage AC output at AC receptacles or outlets 42, or to adjust the DC output of storage device 46 as appropriate for DC receptacles or outlets 38 and/or charging base 40.

When rolling cart 23 is spaced a sufficient distance from the wall surface 20a that contains power transmitter 12 (FIG. 1A), such that there is little or no electrical power coupling between power receiver 16 and power transmitter 12, the receptacles at power receptacle unit 18 are either de-energized (FIG. 1A), or are energized solely by storage device 46 on at least a temporary basis (FIG. 1C). When rolling cart 23 is moved to a location adjacent wall surface 20a so that power receiver 16 is positioned sufficiently close to power transmitter 12 as to form a wireless power coupling, the receptacles at power receptacle unit 18 are energized by electrical power received through electrical power receiver 16, while storage device 46 also receives electrical current from electrical power receiver 16 so that storage device 46 is recharged for later use, such as shown in FIG. 1B. Optionally, an automatic switching device is provided at rolling cart 23, and may be incorporated into the circuitry of power receiver 16, so that power receptacle unit 18 and storage device 46 are both automatically isolated from one another and are both supplied with power from electrical power receiver 16 when the power receiver is sufficiently close to an energized power transmitter 12, and so that power receptacle unit 18 is automatically supplied with power from storage device 46 when power receiver 16 is not receiving power from power transmitter 12.

Optionally, and as shown in FIGS. 2A-2C, wireless electrical power system 10 may be arranged somewhat differently, with power transmitter 12 mounted in floor surface 20b, power receiver 16 mounted externally to a bottom surface of rolling cart 23, and storage device 46 wired in series between power receiver 16 and power receptacle unit 18 via electrical wiring 44, 48. Electrically, the embodiment of FIGS. 2A-2C is substantially the same as that of FIGS. 1A-1C, with power receiver 16 receiving electrical power whenever it is positioned directly above a power transmitter 12 located in floor surface 20b, such as shown in FIG. 2B. This arrangement allows the power receptacle unit 18 to be energized indefinitely when rolling cart 23 is positioned anywhere in work area 22 that a power transmitter 12 is located in the floor surface 20b, and so that cart 23 need not be positioned near a wall surface to receive power. However, when power system 10 includes a storage device 46 as shown, the cart 23 may be positioned substantially anywhere while maintaining power receptacle unit 18 in an energized state, at least until storage device 46 is depleted and requires replacement or recharging.

Figure 3A:
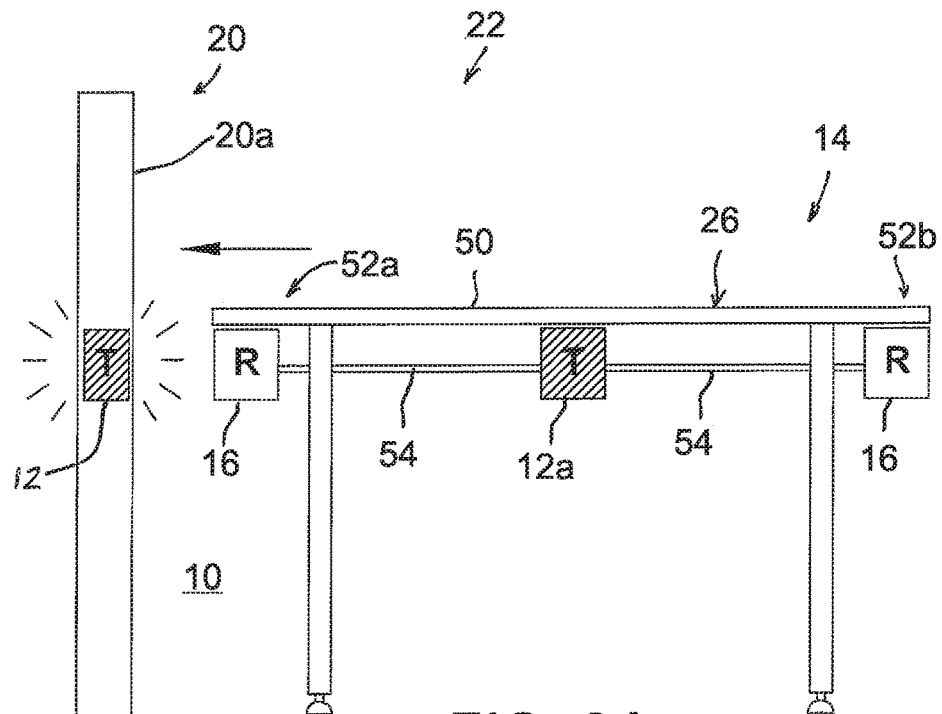
FIG. 3A is a side elevation diagram of a movable table with wireless power receivers and transmitter in accordance with the present invention, shown spaced from a wall surface that is equipped with a wireless power transmitter.
Figure 3B:
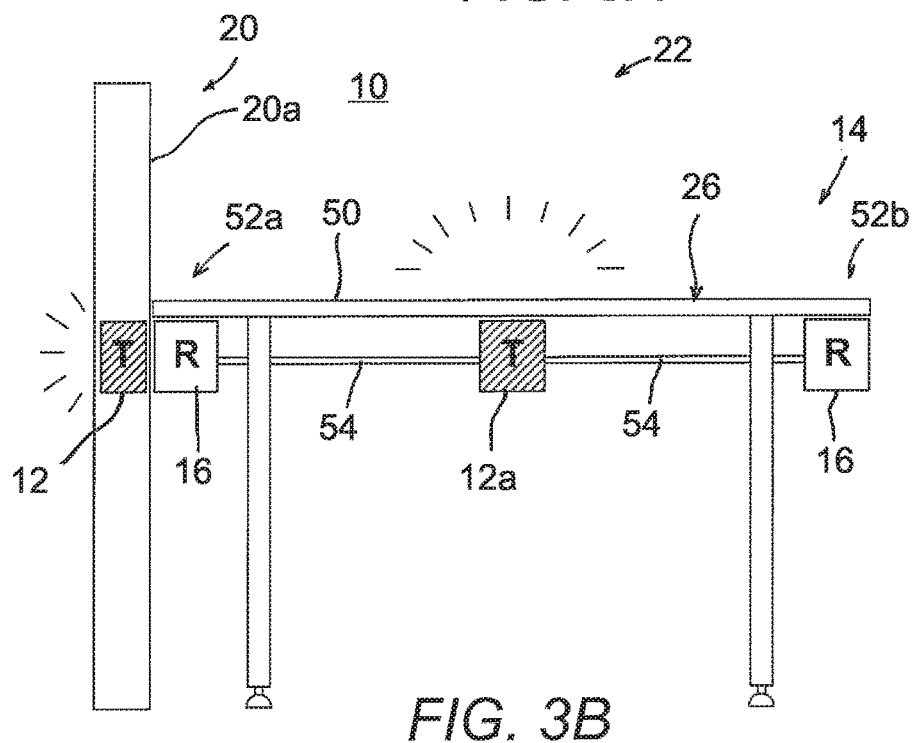
FIG. 3B is another side elevation diagram of the movable table and wall surface of FIG. 3A, in which the table is moved to be adjacent the wall surface.
Figure 5A:
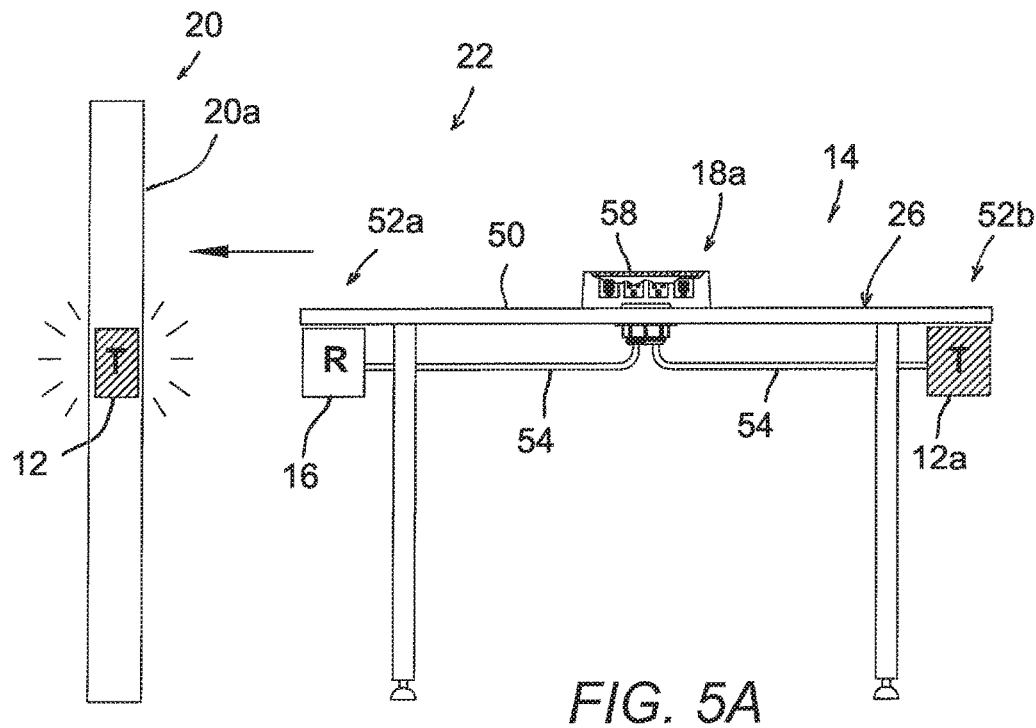
FIG. 5A is a side elevation diagram of another movable table with wireless power receivers and a set of wired power outlets in accordance with the present invention, shown spaced from a wall surface that is equipped with a wireless power transmitter.

Wireless electrical power system 10 may further be arranged in a manner that allows for different arrangements or placement of portable articles 14 that include at least one component acting as a power source for other electrical power consumers. For example, and with reference to FIGS. 3A and 3B, portable desk or table 26 has a top surface 50 and opposite end portions 52a, 52b that are equipped with respective wireless power receivers 16. Table 26 may be slid or moved into a position with first end portions 52a located adjacent wall surface 20a, so that the respective power receiver 16 will form a wireless electrical power coupling with the power transmitter 12 located in wall surface 20a, such as shown in FIG. 3B. It will be appreciated that table 26 could also be rotated 180 degrees about a vertical axis so that the opposite end portion 52b and its corresponding power receiver 16 are adjacent wall surface 20a and power transmitter 12. A centrally-located wireless power transmitter 12a is located under top surface 50 and is electrically coupled to both power receivers 16 via electrical wiring 54. Wireless power transmitter 12a is energizable by either power receiver 16, so that a power consumer positioned along top surface 50, in the vicinity of power transmitter 12a, may be wirelessly energized. Optionally, and in addition to (or in place of) power transmitter 12a, a power receptacle unit may be positioned at or along table 26, such as shown in FIGS. 5A and 5B.

Figure 4A:
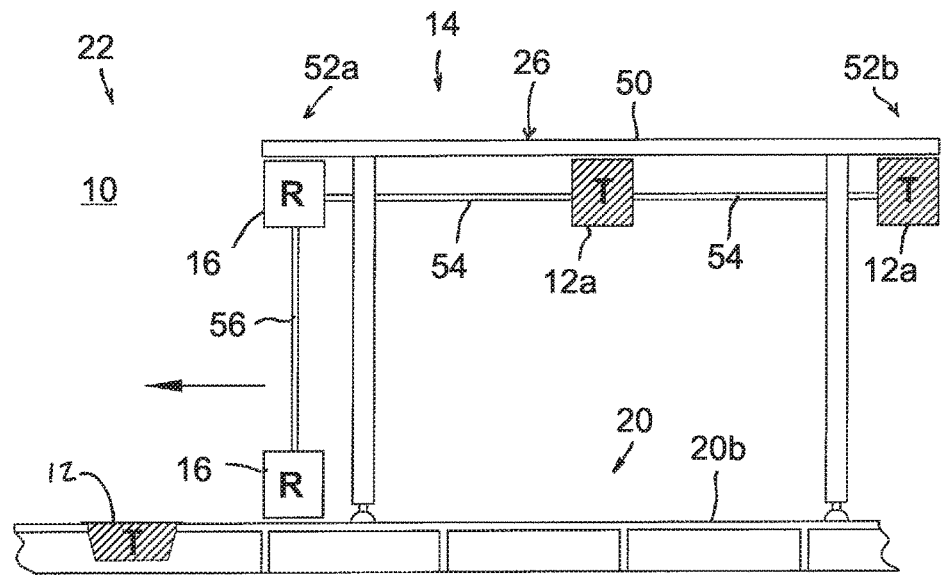
FIG. 4A is a side elevation diagram of another movable table with wireless power in accordance with the present invention, shown positioned along a floor surface and spaced from a wireless power transmitter in the floor surface.
Figure 4B:
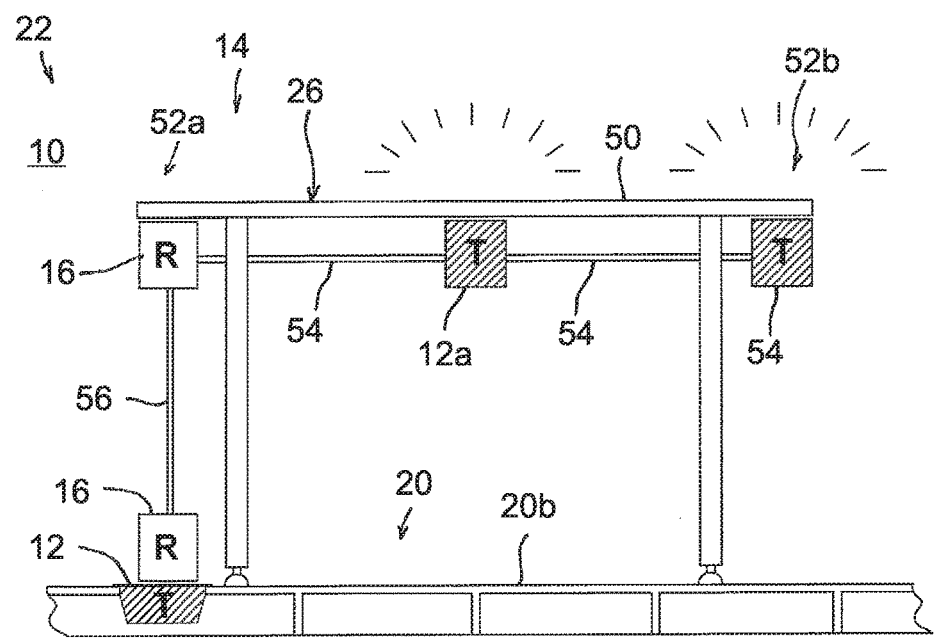
FIG. 4B is another side elevation diagram of the movable table and floor surface of FIG. 4A, in which the cart is moved to align with the wireless power transmitter in the floor surface.

Additional arrangements of power receivers and transmitters are also envisioned, such as those in which portable articles 14 may be configured to receive electrical power from power transmitters 12 in different types of surfaces. For example, desk or table 26 may be equipped with two electrical power receivers 16, a first of which is positioned to form a wireless power coupling with a wall-mounted power transmitter 12, and a second of which is electrically coupled to the first power receiver via wiring 56 and is positioned to form a wireless power coupling with a floor-mounted power transmitter 12, such as shown in FIGS. 4A and 4B. It is further envisioned that multiple power transmitters 12a may be positioned along table 26 or other movable or portable articles 14, thus forming multiple "hot spots" where electrical consumers with their own wireless power receivers can be energized or charged.

Figure 5B:
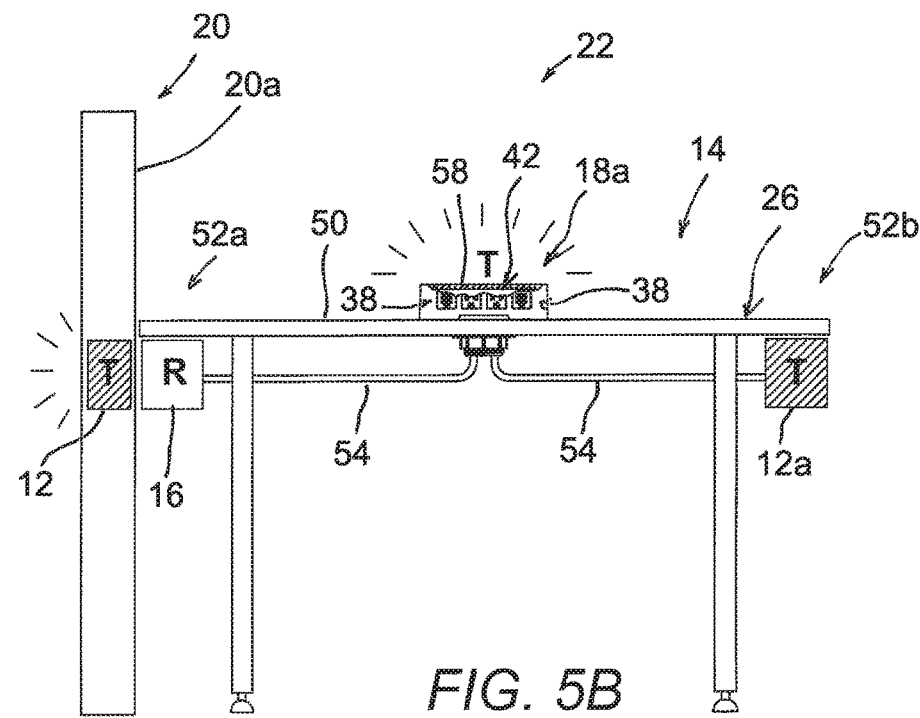
FIG. 5B is another side elevation diagram of the movable table and wall surface of FIG. 5A, in which the table is moved to be adjacent the wall surface.

Optionally, arrangements in which a wireless power receiver 16 is positioned at the first end portion 52a of table 26, and a wireless power transmitter 12a is positioned at the second end portion 52b of table 26 (such as shown in FIGS. 4A-5B), allow multiple tables 26 to be placed in end-to-end or side-by-side arrangement and electrically ganged together via wireless electrical couplings formed by respective power transmitters and receivers of the tables. Such an electrically ganged arrangement is shown in FIGS. 6A and 6B, and will be described below. In the embodiment of FIGS. 5A and 5B, another power receptacle unit 18a is positioned atop the table's top surface 50, and includes high voltage AC receptacles or outlets 42, low voltage DC receptacles or outlets 38, and a low voltage charging pad 58 or a wireless power transmitter.

In the embodiment of FIGS. 6A and 6B, a pair of cabinets 28 are each equipped with one wireless power receiver 16, one wireless power transmitter 12a, and a power receptacle unit 18b including a pair of high voltage AC receptacles or outlets 42, all of which are positioned at a lower end portion 28a of each cabinet 28, so as to align with a power transmitter 12 that is positioned near a lower end of wall surface 20a. As shown in FIG. 6B, each power receptacle unit 18b is energized when the cabinets 18 are placed in close proximity to one another and one of the cabinets is in close proximity to wall surface 20a with its wireless power receiver 16 aligned with the wireless power transmitter 12 of wall surface 20a.

Figure 7C:
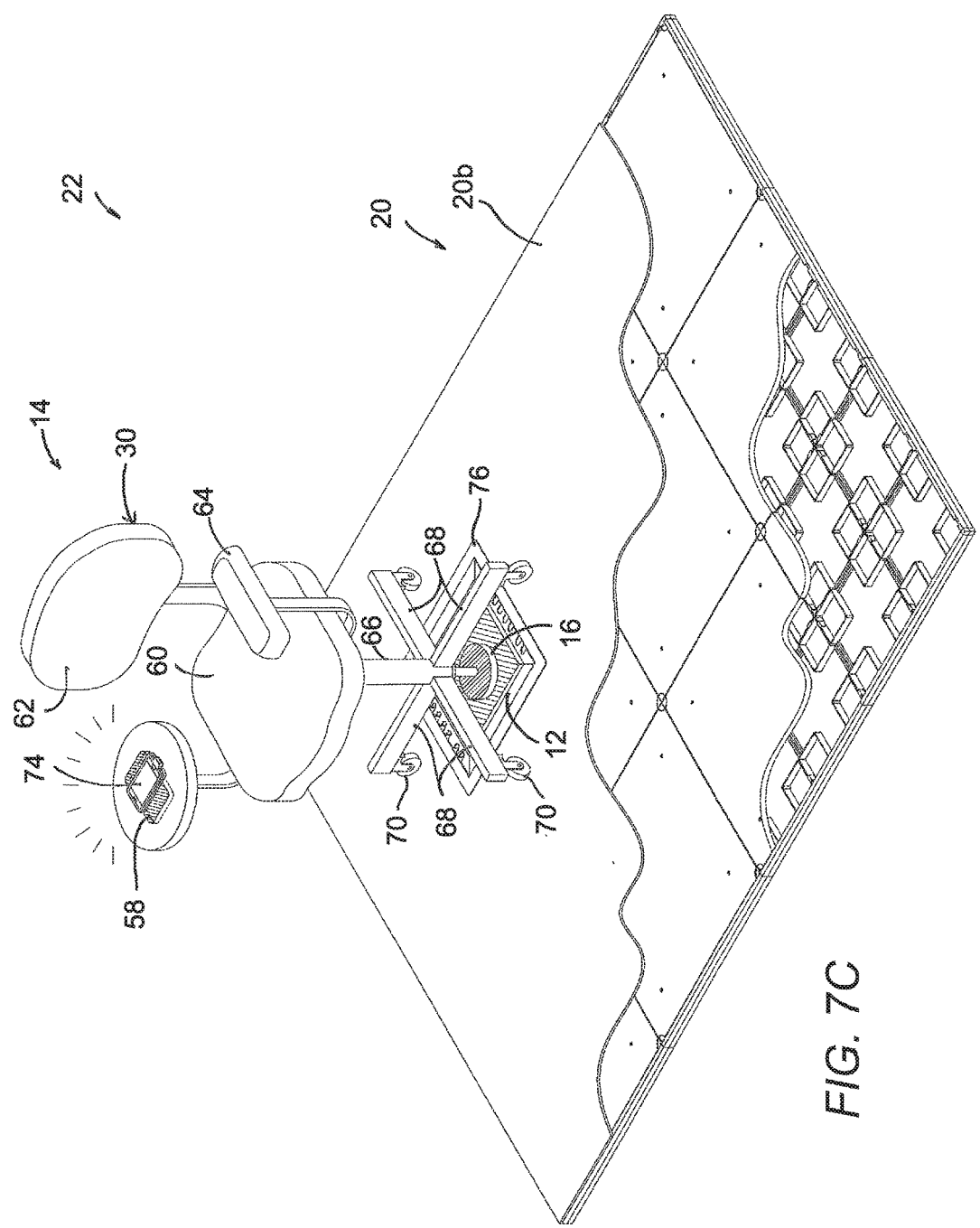
FIG. 7C is another perspective view of the office chair and floor surface of FIG. 7B, in which a portable electronic device is placed on a charging pad of the chair.

Other types of furniture that may incorporate the wireless electrical power system include chairs 30, such as shown in FIGS. 7A-7C. Chair 30 may be substantially conventional in most respects, including a seating surface 60, a seatback 62, one or more armrests 64, a support column 66, support legs 68, and swiveling wheels or casters or rollers 70. Chair 30 further includes a wireless power receiver 16 that extends downwardly from support column 66 a distance so that it is spaced slightly above the floor surface 20b on which wheels 70 rest to support the chair. Chair 30 further includes a combination armrest and writing surface 72, which incorporates a wireless charging pad or transmitter 58 that is electrically energized when the chair is positioned with its power receiver 16 above (and forming a wireless electrical coupling with) an in-floor wireless power transmitter 12, such as shown in FIGS. 7B and 7C. Charging pad or transmitter 58 is configured to supply electrical power to a power consumer 74 that is resting on the pad or transmitter 58, such as shown in FIG. 7C. Similar charging pads are disclosed and more fully described in co-pending and commonly-owned U.S. patent application Ser. No. 13/385,008, filed Jan. 27, 2012 (U.S. Publication No. 2012/0200989), which is hereby incorporated herein by reference in its entirety. Suitable charging pad technologies are also marketed and sold by Pure Energy Solutions, Inc. of Boulder, Colo., for example. Optionally, the chair may also include AC power outlets and/or DC power outlets at a location that is convenient to a person seated at the chair. Power consumer 74 may be a wireless phone, a hand-held or laptop computer, or substantially any electrical or electronic device that is supportable on armrest and writing surface 72.

Figure 8A:
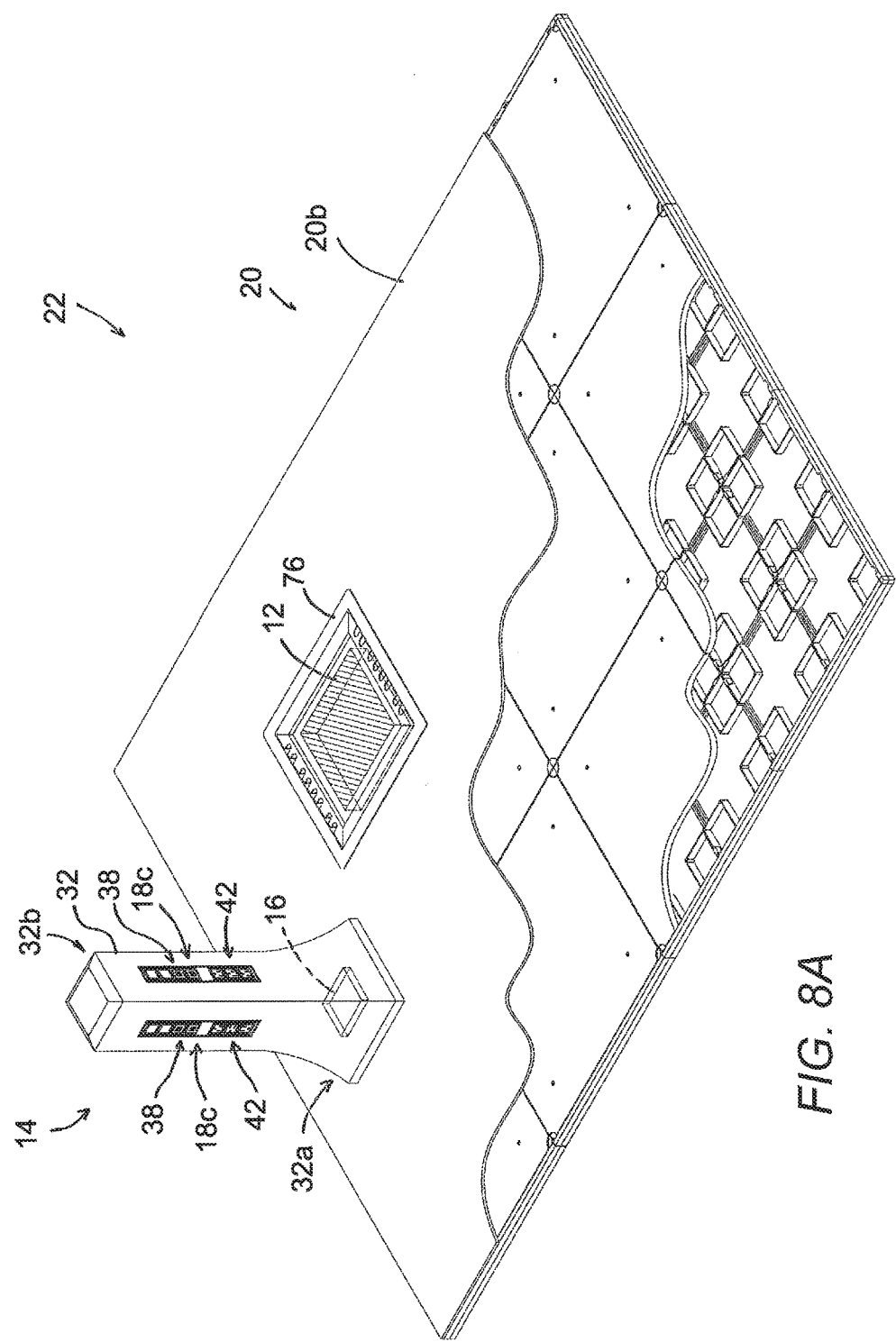
FIG. 8A is a perspective view of a movable tower with wireless power capability in accordance with the present invention, shown positioned along a floor surface and spaced from a wireless power transmitter in the floor surface.
Figure 8B:
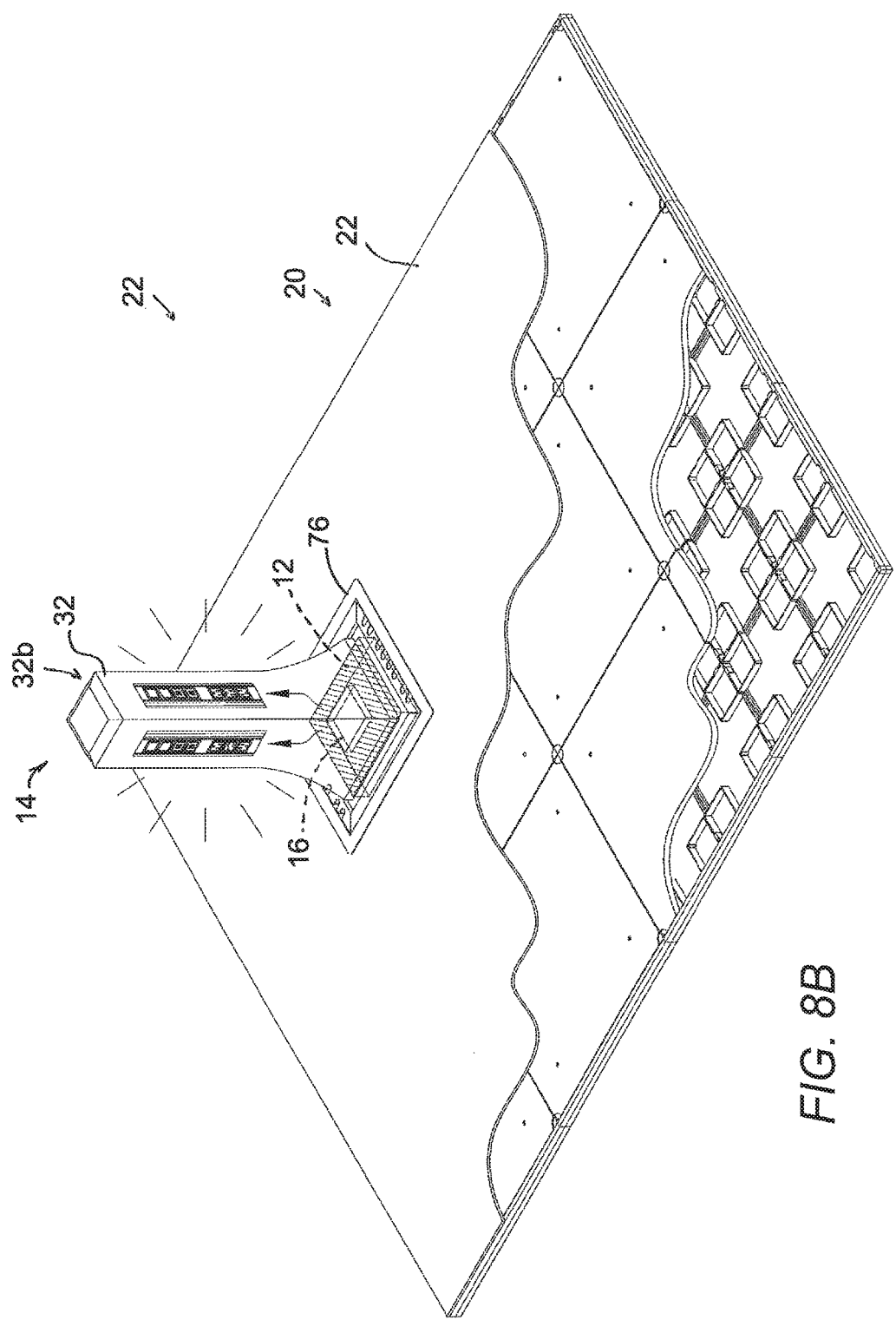
FIG. 8B is another perspective view of the tower and floor surface of FIG. 8A, in which the tower is aligned with the wireless power transmitter in the floor surface.

Similar to chair 30 of FIGS. 7A-7C, the rolling cart 23 of FIGS. 2A-2C, and the table 26 of FIGS. 4A and 4B, movable tower 32 is energizable by placing it atop a power transmitter 12 located in floor surface 20b (FIGS. 8A and 8B). In the illustrated embodiment, movable tower 32 includes at least two power receptacle units 18c including high voltage AC receptacles 42 and low voltage DC receptacles 38, and has a power receiver 16 mounted at a lower end portion 32a. Optionally, an upper end portion 32b houses a wireless charging pad or transmitter. Accordingly, work areas 22 having multiple wireless power transmitters 12 located in wall surfaces 20a, floor surfaces 20b, or ceiling surfaces 20d may be readily reconfigured by relocating different types of portable articles, such as furniture, in locations where the power systems associated with the articles will be energized as desired, and substantially without need for any visible or obstructive wiring.

It will be appreciated that any of the portable articles 14, including (but not necessarily limited to) desk or table 26, cabinet 28, chair 30, movable tower 32, table-supportable electrified monuments 34a, 34b, and electric portable lamp 36 may include or incorporate an electrical energy storage device similar to storage device 46 described above with reference to rolling cart 23. The electrical energy storage device would be sized and shaped as appropriate for packaging purposes within the available space in or along the portable article and the desired electrical output and storage capacity for the storage device.

In the illustrated embodiments of 4A, 4B, and 7A-8B, floor surface 20b is a raised floor surface with electrical wiring routed underneath, and with wireless power transmitter 12 mounted in a floor box 76. Such raised floor surfaces, wiring arrangements, and floor boxes are more fully described in commonly-owned U.S. Pat. Nos. 7,878,845 and 7,183,504, which are hereby incorporated herein by reference in their entireties.

Optionally, portable articles 14 that incorporate the wireless electrical power system of the present invention may include different types of electrical devices that are configured to be supported on a work surface such as a table or desk 26, and that include one or more power outlets, light sockets, or the like. For example, and with reference to FIGS. 9A-10B, table 26 includes a circular wireless power transmitter 12b that is similar to the wireless power transmitter 12a of FIGS. 3A-4B, but which is directly electrically coupled to an electrical outlet, such as a conventional high voltage AC wall outlet 78, via a conventional power cord 80 with plug 82 (FIGS. 9A and 9B). Table-supported monument 34a operates in substantially the same manner along table 26 as does tower 32 along floor surface 20b, with the monument's high voltage AC receptacle(s) or outlet(s) 42 and low voltage DC receptacle(s) or outlet(s) 38 being energized whenever the monument 34a is placed directly above an energized wireless power transmitter 12b, so that the transmitter 12b and the monument's wireless power receiver 16 form a wireless electrical coupling, such as shown in FIGS. 9B and 10B.

Figure 12A:
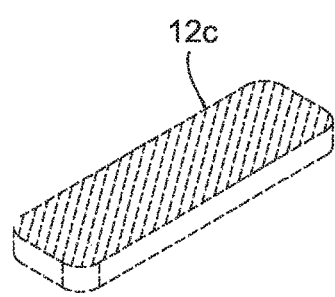
FIG. 12A is a perspective view of a generally rectangular power transmitter.
Figure 12B:
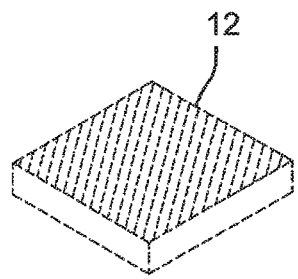
FIG. 12B is a perspective view of a square power transmitter.

Optionally, the portable articles 14 may take any number of different forms and/or shapes, without departing from the spirit and scope of the present invention. For example, table-supported monuments may have different dimensions to accommodate different types and numbers of electrical outlets or other features, such as the rectangular four-outlet monument 34b of FIG. 11A and the portable lamp 36 with low voltage receptacles 38 and high voltage receptacles or outlets 42 (FIG. 11B). The size and shape of each wireless power transmitter and each wireless power receiver may also be varied according to application, such as power requirements and the desired size of a "hot zone" in which a portable article 14 may be located for establishing a sufficient wireless power coupling. For example, four-outlet monument 34b and portable lamp 36 each incorporate a respective elongate and generally rectangular wireless power receiver 16c (FIGS. 11A and 11B), which corresponds to an elongate and generally rectangular wireless power transmitter 12c (FIG. 12A). Substantially any size or shape of power receiver and power transmitter is envisioned, with one size or shape of wireless power receiver being compatible with more than one size or shape of wireless power transmitter. For example, a generally square wireless power receiver 16 may be compatible with the circular wireless power transmitter 12b, such as shown in FIGS. 9A and 9B.

Various additional features are envisioned that may enhance or facilitate the use of the wireless electrical power system. For example, each portable article 14 may include an indicator light that illuminates when a sufficient wireless electrical coupling has been established between a wireless power transmitter and at least one wireless power receiver of the portable article. Optionally, such indications can be made with one or more audible tones generated by a loudspeaker incorporated into the portable article. It is also envisioned that the portable articles may be fitted with magnets that cooperate with corresponding magnets near compatible wireless power transmitters, to provide users with a sensory indication that a sufficient wireless electrical coupling has been established, and which may also help to retain the portable article in its wirelessly electrically coupled position. Surfaces on the portable articles may also be shaped to engage corresponding surfaces at or near compatible wireless power transmitters, such as a shallow recess formed in a table or other work surface at the location of a wireless power transmitter, where the shallow recess is sized and shaped to receive the lower portion of a compatible electrified monument.

Accordingly, the wireless electrical power system of the present invention provides users with numerous options to configure and relocate various types of electrical outlets and/or wireless power transmitters, charging pads, or the like, simply by selecting and positioning desired portable articles (such as furniture and electrical devices) that incorporate the desired electrical outlets or other electrical components. In addition to providing users with reconfigurable access to electrical power, the selected portable articles may provide additional functions such as seating, storage, work surfaces, etc., or combinations thereof. Work areas incorporating the wireless electrical power system are quickly reconfigurable by moving or replacing the portable articles in a manner that meets new functional and electrical needs of the work area.

Changes and modifications in the specifically-described embodiments may be carried out without departing from the principles of the present invention, which is intended to be limited only by the scope of the appended claims as interpreted according to the principles of patent law including the doctrine of equivalents.

The embodiments of the invention in which an exclusive property or privilege is claimed are defined as follows:

1. A wireless electrical power system for use in a work area, said system comprising:
   a first wireless electrical power transmitter disposed in a surface that defines a portion of a work area;
   a portable article configured to be positioned within the work area and movable between two or more locations in the work area;
   a plurality of wireless electrical power receivers positioned at said portable article and configured such that a first of said wireless electrical power receivers receives electrical power from said first wireless electrical power transmitter when said first wireless electrical power receiver is adjacent or spaced from said first wireless electrical power transmitter by a distance that is less than or equal to a maximum transmission distance, wherein a second of said plurality of wireless electrical power receivers is positioned on a same side of said portable article and above said first wireless electrical power receiver; and
   a second wireless electrical power transmitter positioned at said portable article, wherein said second wireless electrical power transmitter is configured to (i) receive electrical power directly from one of the plurality of wireless electrical power receivers, and (ii) provide electrical power to another wireless electrical power receiver of an electrical device positioned at said portable article when said another wireless electrical power receiver is adjacent or spaced from the second wireless electrical power transmitter by a distance that is less than or equal to a maximum transmission distance.

2. The wireless electrical power system of claim 1, wherein said second wireless electrical power receiver receives electrical power from said first wireless electrical power transmitter when said second wireless electrical power receiver is adjacent or spaced from said first wireless electrical power transmitter by a distance that is less than or equal to a maximum transmission distance.

3. The wireless electrical power system of claim 1, further in combination with the electrical device, wherein said electrical device comprises an electrical outlet configured to (i) receive electrical power directly from said another wireless electrical power receiver of said electrical device, and (ii) provide electrical power to an electrical consumer that is electrically coupled to said electrical outlet.

4. The wireless electrical power system of claim 3, wherein said electrical outlet comprises a high voltage AC electrical outlet and a low voltage DC electrical outlet.

5. The wireless electrical power system of claim 1, further in combination with the electrical device, wherein said electrical device comprises a lamp.

6. The wireless electrical power system of claim 1, wherein said another wireless electrical power receiver is configured to have one of a circular, square, and elongated shape.

7. The wireless electrical power system of claim 1, wherein said second wireless electrical power transmitter comprises a plurality of wireless electrical power transmitters spaced apart from each other and positioned at said portable article.

8. The wireless electrical power system of claim 7, further in combination with the electrical device, wherein said electrical device is configured to be movable between said plurality of wireless electrical power transmitters.

9. The wireless electrical power system of claim 1, wherein said first wireless electrical power transmitter comprises an inductive power transmitter that receives electrical power via wiring from a main power source associated with the work area.

10. The wireless electrical power system of claim 9 further in combination with the surface that defines a portion of a work area, wherein said surface that defines a portion of a work area is one of: (i) a wall or divider surface, (ii) a floor surface, (iii) a work surface, and (iv) a ceiling surface.

11. The wireless electrical power system of claim 1, wherein said portable article comprises a table.

12. A wireless electrical power system for use in a work area, said system comprising:

a portable article configured to be positioned within the work area and movable between two or more locations in the work area;

an electrical device configured to be positioned at said portable article and comprising a wireless electrical power receiver;

a wireless electrical power transmitter positioned at said portable article and configured to (i) receive electrical power directly from a first electrical outlet via a conventional power cord with a plug, and (ii) provide electrical power to said wireless electrical power receiver of said electrical device when said wireless electrical power receiver is adjacent or spaced from said wireless electrical power transmitter by a distance that is less than or equal to a maximum transmission distance; and wherein said electrical device comprises a second electrical outlet configured to (i) receive electrical power directly from said wireless electrical power receiver, and (ii) provide electrical power to an electrical consumer that is electrically coupled to said second electrical outlet.

13. The wireless electrical power system of claim 12, wherein said electrical device comprises a lamp.

14. The wireless electrical power system of claim 12, wherein said wireless electrical power receiver of said electrical device is configured to have one of a circular, square, and elongated shape.

15. The wireless electrical power system of claim 12 further comprising a plurality of said wireless electrical power transmitters spaced apart from each other and positioned at said portable article.

16. The wireless electrical power system of claim 15, wherein said electrical device is movable between said plurality of wireless electrical power transmitters and configured to receive electrical power from any of said plurality of said wireless electrical power transmitters.

17. The wireless electrical power system of claim 12, wherein said second electrical outlet comprises an AC electrical outlet, and said electrical device further comprises a DC electrical outlet.

18. The wireless electrical power system of claim 17, wherein said AC electrical outlet is a high voltage AC outlet, and wherein said DC electrical outlet is a low-voltage DC outlet.

19. The wireless electrical power system of claim 12, wherein said portable article comprises a table.

* * * * *